(12) United States Patent
Hoshino

(10) Patent No.: US 8,754,183 B2
(45) Date of Patent: Jun. 17, 2014

(54) WATER/OIL REPELLENT AGENT AND WATER/OIL REPELLENT COMPOSITION

(71) Applicant: Asahi Glass Company, Limited, Chiyoda-ku (JP)

(72) Inventor: Taiki Hoshino, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 13/693,654

(22) Filed: Dec. 4, 2012

(65) Prior Publication Data

US 2013/0092047 A1   Apr. 18, 2013

Related U.S. Application Data

(63) Continuation of application No. PCT/JP2011/062730, filed on Jun. 2, 2011.

(30) Foreign Application Priority Data

Jun. 4, 2010 (JP) .................................. 2010-129012

(51) Int. Cl.
   C08G 18/28 (2006.01)
(52) U.S. Cl.
   USPC .......... 528/70; 528/49; 528/73; 528/76; 528/80; 528/85; 524/590; 524/589; 524/591
(58) Field of Classification Search
   USPC ............ 528/49, 70, 73, 76, 80, 85; 524/589, 524/590, 591; 428/423.4, 423.5, 423.1, 428/423.7, 423.9
   See application file for complete search history.

(56) References Cited

U.S. PATENT DOCUMENTS

| 4,382,798 A | * | 5/1983 | Suzuki et al. ............... 8/94.1 R |
| 4,539,006 A | * | 9/1985 | Langford .................... 8/94.1 R |
| 2009/0148654 A1 | * | 6/2009 | Brown et al. ................. 428/96 |
| 2012/0085960 A1 | | 4/2012 | Hoshino et al. |

FOREIGN PATENT DOCUMENTS

| JP | 58-189284 | | 11/1983 |
| JP | 62-181385 | | 8/1987 |
| JP | 4-26658 | | 1/1992 |
| JP | 6-287514 | | 10/1994 |
| JP | 2001-329038 | | 11/2001 |
| JP | 2001329038 | * | 11/2001 |
| WO | 2006/013791 | | 2/2006 |
| WO | 2007/002894 | | 1/2007 |
| WO | 2009/087981 | | 7/2009 |

OTHER PUBLICATIONS

English translation of document N.*
International Search Report issued Aug. 16, 2011 in PCT/JP2011/062730 filed Jun. 2, 2011.

* cited by examiner

*Primary Examiner* — Michael L Leonard
(74) *Attorney, Agent, or Firm* — Oblon, Spivak, McClelland, Maier & Neustadt, L.L.P.

(57) ABSTRACT

To provide a water/oil repellent agent and a water/oil repellent composition which are capable of imparting sufficient water/oil repellency to the surface of an article and which have low environmental impact. One comprising a reaction product obtained by reacting a fluorinated alcohol or amine having a polyfluoroalkyl moiety having at most 6 carbon atoms with a polyisocyanate compound, which is, when applied to an article, capable of imparting sufficient water/oil repellency, while presenting little environmental impact. When applied to an article, the water/oil repellent composition of the present invention is capable of imparting a high quality water/oil repellency to the article.

10 Claims, No Drawings

WATER/OIL REPELLENT AGENT AND WATER/OIL REPELLENT COMPOSITION

TECHNICAL FIELD

The present invention relates to a water/oil repellent agent and a water/oil repellent composition.

BACKGROUND ART

As a method for imparting water/oil repellency to the surface of an article (such as a fiber product), a method of treating the article by means of a water/oil repellent composition composed of a solution having dissolved in or an emulsion having dispersed in a medium, a variable fluorinated compound having a polyfluoroalkyl group, particularly a fluorinated urethane compound or a fluoropolymer, has been known.

In Patent Document 1 or 2, as a fluorinated urethane compound having a polyfluoroalkyl group, a fluorinated urethane compound which is a reaction product of a polyisocyanate and a fluorinated alcohol having a polyfluoroalkyl group having at least 8 carbon atoms (including other alcohols) has been used.

However, recently, EPA (US Environmental Protection Agency) has pointed out that a compound having a perfluoroalkyl group having at least 8 carbon atoms is likely to be decomposed in the environment or in vivo, and the decomposition product is likely to be accumulated, i.e. it presents high environmental impact. Therefore, a water/oil repellent composition has been required which has a polyfluoroalkyl group having at most 6 carbon atoms.

Patent Document 3 discloses a fluorinated urethane compound which is a reaction product of a fluorinated alcohol having a perfluoroalkyl group having 4 carbon atoms and a sulfonyl group, and a polyisocyanate, for reducing the environmental impact. However, the water/oil repellency of articles treated with a water/oil repellent composition comprising the above reaction product is insufficient.

Patent Document 4 discloses a urethane compound which is formed by a reaction of a fluoroacryl oligomer having a perfluoroalkyl group having at most 4 carbon atoms and a hydroxyl group at its terminal, and a polyisocyanate. For the production of the urethane compound, two steps are required, i.e. a step of polymerization for forming an oligomer having a functional group which is reactive to an isocyanate at a terminal and a step of reacting the oligomer and an isocyanate. Thus, such a production process is complicated.

PRIOR ART DOCUMENTS

Patent Documents

Patent Document 1: JP-A-58-189284
Patent Document 2: JP-A-62-181385
Patent Document 3: WO2006/013791
Patent Document 4: WO2007/002894

DISCLOSURE OF INVENTION

Technical Problem

It is an object of the present invention to provide a water/oil repellent agent and a water/oil repellent composition which are capable of imparting sufficient water/oil repellency to a surface of an article and which have low environmental impact.

Solution to Problem

The present invention provides the following water/oil repellent agent and water/oil repellent composition.

[1] A water/oil repellent agent which comprises a reaction product of the following fluorinated compound (a) with a polyisocyanate compound (b):

$$R^f\text{—X—Ph—Y—Z} \qquad \text{Fluorinated compound (a)}$$

wherein $R^f$ is a $C_{1-6}$ polyfluoroalkyl group, X is a single bond, a $C_{1-4}$ alkylene group, $(CH_2)_mO(CH_2)_n$ (each of m and n which are independent of each other, is an integer of from 0 to 4) or $(CH_2)_pOCO$ (p is an integer of from 1 to 4), Ph is a phenylene group, Y is a single bond, a $C_{1-4}$ alkylene group or $(CH_2)_qO(CH_2)_r$ (q is an integer of from 0 to 4, and r is an integer of from 1 to 4), and Z is OH or NHR (R is a hydrogen atom or a $C_{1-6}$ alkyl group).

[2] The water/oil repellent agent according to [1], wherein the reaction product has no isocyanate group.

[3] The water/oil repellent agent according to [1] or [2], wherein the $R^f$ in the fluorinated compound (a) is a $C_{4-6}$ perfluoroalkyl group.

[4] The water/oil repellent agent according to any one of [1] to [3], wherein the fluorinated compound (a) is a fluorinated compound represented by the following formula (a1) or (a2):

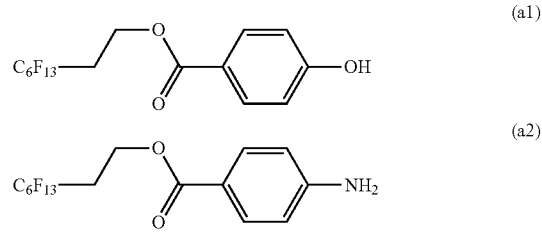

[5] The water/oil repellent agent according to any one of [1] to [4], wherein the polyisocyanate compound (b) is hexamethylene diisocyanate or its modified product.

[6] A water/oil repellent composition which comprises the water/oil repellent agent as defined in any one of [1] to [5] and a solvent.

Advantageous Effects of Invention

The water/oil repellent agent of the present invention does not contain a perfluoroalkyl group having at least 8 carbon atoms, whereby it is safe and has low environmental impact without generation of a perfluorooctanoic acid (PFOA), and it is capable of imparting sufficient water/oil repellency to the surface of an article.

The water/oil repellent composition of the present invention is capable of imparting sufficient water/oil repellency to the surface of an article and has low environmental impact.

DESCRIPTION OF EMBODIMENTS

The water/oil repellent agent of the present invention comprises a reaction product of the fluorinated compound (a), the polyisocyanate compound (b) and, as the case requires, a compound (c).

<Fluorinated Compound (a)>

In the present invention, the fluorinated compound (a) is a fluorinated alcohol or fluorinated amine having a phenylene group, which is represented by the following formula (I), and two or more of such compounds may be used in combination.

wherein $R^f$ is a $C_{1-6}$ polyfluoroalkyl group, X is a single bond, a $C_{1-4}$ alkylene group, $(CH_2)_mO(CH_2)_n$ (each of m and n which are independent of each other, is an integer of from 0 to 4) or $(CH_2)_pOCO$ (p is an integer of from 1 to 4), Ph is a phenylene group, Y is a single bond, a $C_{1-4}$ alkylene group or $(CH_2)_qO(CH_2)_r$ (q is an integer of from 0 to 4, and r is an integer of from 1 to 4), and Z is OH or NHR (R is a hydrogen atom or a $C_{1-6}$ alkyl group).

A polyfluoroalkyl group is an alkyl group having the majority of hydrogen atoms substituted by fluorine atoms. $R^f$ is preferably a perfluoroalkyl group having all hydrogen atoms bonded to carbon substituted by fluorine atoms, and it is more preferably a $C_{4-6}$ linear perfluoroalkyl group.

In the above formula (I), X is a single bond, a $C_{1-4}$ alkylene group, $(CH_2)_mO(CH_2)_n$ (each of m and n which are independent of each other, is an integer of from 0 to 4) or $(CH_2)_pOCO$ (p is an integer of from 1 to 4).

In the above formula (I), Ph is a phenylene group. It may be any one of a 1,2-phenylene group, a 1,3-phenylene group and a 1,4-phenylene group, so long as it is a phenylene group, and a hydrogen atom in the phenylene group may be substituted by a substituent. Such a substituent is not particularly limited, but from the viewpoint of the synthesis, one having a low reactivity is preferred, and an alkyl group, an alkoxy group, an acyl group, a cyano group or a nitro group, may, for example, be exemplified. In the present invention, Ph is preferably a 1,4-phenlene group from the viewpoint of the availability of the raw material.

In the above formula (I), Y is a single bond, a $C_{1-4}$ alkylene group or $(CH_2)_qO(CH_2)_r$ (q is an integer of from 0 to 4, and r is an integer of from 1 to 4).

In the above formula (I), Z is OH or NHR (R is a hydrogen atom or a $C_{1-6}$ alkyl group).

In the present invention, among the fluorinated compounds (a) represented by the above formula (I), a compound represented by the following formula (a1) or (a2) is particularly preferred, since it is capable of imparting water/oil repellency to the surface of an article.

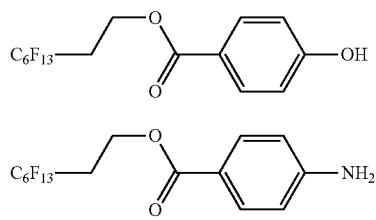

In the water/oil repellent agent of the present invention, when the fluorinated compound (a) is a fluorinated alcohol, it is reacted with a polyisocyanate compound (b) to form a fluorinated urethane compound, and when it is a fluorinated amine, it is reacted with a polyisocyanate compound (b) to form a fluorinated urea compound.

In the present invention, the method for producing the fluorinated compound (a) is not particularly limited. For example, it may be produced by the following production method.

Using a compound represented by the formula $X^1OCOPhZ^1$ (wherein $X^1$ is a hydrogen atom or a $C_{1-4}$ alkyl group, and $Z^1$ is a hydrogen atom or an amino group) as a starting material, it is reacted with a compound having an $R^F$ group as shown by the following reaction formula to obtain a compound (a1) or (a2).

In the above reaction, it is preferred to use, as a catalyst, an acid such as 4-toluenesulfonic acid monohydrate or sulfuric acid, or a base such as potassium carbonate or triethylamine. The reaction may be carried out in the absence of a solvent or in a solvent, and particularly, it is possible to use, for example, toluene or 2-butanone.

With respect to proportions of the catalyst and the solvent, it is preferred that the catalyst is from 0.01 to 10 parts by mass, and the solvent is from 0 to 5,000 parts by mass, based on 100 parts by mass of the total amount of the above starting material and $C_6F_{13}C_2H_4OH$.

The reaction conditions may preferably be such conditions that the reactor is made of e.g. glass or SUS, the temperature is from 50 to 150° C., the pressure is from −0.1 to 1 MPa, the atmosphere is substituted by a gas such as nitrogen or argon, and the time is from 1 to 100 hours. Further, if necessary, it is preferred to carry out the reaction while distilling off reaction byproducts.

Further, the compound (a1) or (a2) may be purified from the crude reaction solution obtained by the above reaction. The purification method may, for example, be a method wherein excess raw material components are distilled off from the crude reaction solution, and to the residue, methanol, chloroform or the like is added to recrystallize the compound (a1) or (a2), or a method wherein excess raw material components are distilled off from the crude reaction solution, then dichloropentafluoropropane, chloroform, ethyl acetate or the like is added to the residue, followed by washing a few times with a sufficient amount of distilled water, and then the solvent is distilled off.

<Polyisocyanate Compound (b)>

In the present invention, the polyisocyanate compound (b) is a compound having at least two isocyanate groups. The polyisocyanate compound (b) may, for example, be an aliphatic, alicyclic or aromatic polyisocyanate having at least two isocyanate groups, a mixture of two or more such polyisocyanates, or modified polyisocyanates obtainable by modifying them.

The aliphatic, alicyclic or aromatic polyisocyanate having at least two isocyanate groups may, for example, be hexamethylene diisocyanate (HDI), isophorone diisocyanate (IPDI), tolylene diisocyanate (TDI), diphenylmethane diisocyanate (MDI), polymethylenepolyphenyl polyisocyanate (so-called crude MDI or polymeric MDI) or xylylene diisocyanate (XDI).

The modified polyisocyanate may, for example, be a prepolymer type modified product, nurate modified product, biuret modified product, urethane modified product, urea modified product or carbodiimide modified product of the above polyisocyanate.

In the present invention, the polyisocyanate compound (b) is particularly preferably hexamethylene diisocyanate or its modified product, from the viewpoint of the solubility of the water/oil repellent agent thereby obtainable.

The content of isocyanate groups in the polyisocyanate compound (b) is preferably from 5 to 40 mass %, more preferably from 10 to 30 mass %, most preferably from 15 to 30 mass %.

<Compound (c)>

The reaction product in the present invention may further contain a reaction product of a polyisocyanate compound (b) with a compound (c) having an active hydrogen group reactive with an isocyanate group, or a reaction product of a polyisocyanate (b) with the fluorinated compound (a) and a compound (c) having an active hydrogen group reactive with an isocyanate group.

The active hydrogen group may, for example, be a hydroxy group, an amino group or a mercapto group. Further, it may be a blocking agent capable of blocking an isocyanate group. Further, it may be water. When an isocyanate group is reacted with water, an amino group will be formed by hydrolysis, and the formed amino group will be further reacted with another isocyanate to form a urea bond, whereby it is possible to introduce a crosslinked structure in the molecule.

In the present invention, the reaction product is preferably one wherein the compound (c) is reacted preferably from 0 to 50%, more preferably from 0 to 30%, to isocyanate groups in the polyisocyanate compound (b). By incorporating the reaction product with the compound (c) by properly adjusting the proportion in such a range, it is possible to impart another properties without substantially impairing the effects of the water/oil repellent agent of the present invention (excellent in water/oil repellency with low environmental impact). As the compound (c), two or more types may be used.

In the present invention, the compound (c) may, for example, be a compound having one active hydrogen group, such as an alcohol having a polyfluoroalkyl group, a linear or branched alkyl alcohol, an alcohol having a functional group other than a hydroxy group, an alcohol-modified silicone or an alcohol having a polyoxyalkylene chain. Further, it may be a compound (polyhydric alcohol) having a plurality of active hydrogen groups, or a blocking agent. As the compound (c), among them, a compound having one active hydrogen group is particularly preferred, since it is capable of improving the solubility of the water/oil repellent agent in a solvent.

As the compound (c), specifically, a monohydric alcohol may, for example, be $CF_3CH_2OH$, $C_2F_5CH_2OH$, $C_2F_5C_3H_6OH$, $C_4F_9CH_2OH$, $HC_2F_4CH_2OH$, $C_6F_{13}CH_2OH$, $C_4F_9C_2H_4OH$, $C_6F_{13}C_2H_4OH$, $C_4F_9C_3H_6OH$, $C_6F_{13}C_3H_6OH$, $C_4F_9SC_2H_4OH$, $C_6F_{13}SC_2H_4OH$, $C_4F_9SO_2C_2H_4OH$, $C_6F_{13}SO_2C_2H_4OH$, $C_4F_9C_2H_4SC_2H_4OH$, $C_6F_{13}C_2H_4SC_2H_4OH$, $C_4F_9C_2H_4SO_2C_2H_4OH$, $C_6F_{13}C_2H_4SO_2C_2H_4OH$, $C_4F_9SO_2N(CH_3)C_2H_4OH$, $C_6F_{13}SO_2N(CH_3)C_2H_4OH$, methanol, ethanol, 1-propanol, 2-propanol, 1-butanol, 2-butanol, 2-methyl-1-butanol, tert-butanol, 1-hexanol, 2-ethylhexanol, 1-octanol, lauryl alcohol, cetyl alcohol, stearyl alcohol, behenyl alcohol, ethylene glycol monoacetate, propylene glycol monoacetate, diethylene glycol monoacetate, dipropylene glycol monoacetate, triethylene glycol monoacetate, polyethylene glycol monoacetate, ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, polyethylene glycol monoethyl ether, hydroxpcetone, 4-hydroxy-2-butanone or one terminal alcohol-modified silicone.

A compound having one amino group as an active hydrogen group may, for example, be methylamine, ethylamine, propylamine, butylamine, hexylamine, octylamine, dodecylamine, cetylamine, stearylamine, behenylamine, diethylamine or dibutylamine.

A polyhydric alcohol may, for example, by ethylene glycol, propylene glycol, trimethylene glycol, 1,4-butanediol, 2,3-butanediol, 1,5-pentanediol, 1,6-hexanediol, diethylene glycol, triethylene glycol, tetraethylene glycol, polyethylene glycol, dipropylene glycol, glycerin, pentaerythritol, dipentaerythritol, monosaccharide, disaccharide or oligosaccharide.

A compound containing an amino group may, for example, be ethylenediamine, propylenediamine or hexamethylenediamine.

The blocking agent may, for example, be 3,5-dimethylpyrazole, acetoxime, methyl ethyl ketoxime, benzophenone oxime, thiophenol, hydroxylamine, primary aminomercaptan or secondary aminomercaptan. Particularly preferred is methyl ethyl ketoxime or 3,5-dimethylpyrazole.

As the compound (c), one of the above-mentioned may be used alone, or two or more of them may be used in combination.

<Production Method for Reaction Product>

The reaction product in the present invention is obtainable by reacting the fluorinated compound (a) with the polyisocyanate compound (b). In the case of reacting also a compound (c) in addition to the fluorinated compound (a), the fluorinated compound (a) and the compound (c) may sequentially be reacted with the polyisocyanate compound (b), or a mixture of the fluorinated compound (a) and the compound (c) may be reacted thereto. At that time of reaction, a catalyst and a solvent for the reaction may suitably be used.

In a case where Z in the fluorinated compound (a) is an amino group ($NH_2$), depending upon the reaction conditions, the reaction product in the present invention may contain a reaction product having the compound further reacted with a hydrogen atom of an urethane bond or urea bond of the formed product.

In the present invention, the proportions of the fluorinated compound (a) and the polyisocyanate compound (b) are preferably adjusted so that the molar ratio of active hydrogen groups (hydroxy groups, amino groups, mercapto groups, etc.) in the fluorinated compound (a) to isocyanate groups in the polyisocyanate compound (b) becomes 1:1. In a case where the compound (c) is also reacted, it is preferred to adjust the proportions so that the molar ratio of the total of active hydrogen groups in the fluorinated compound (a) and the compound (c) to isocyanate groups in the polyisocyanate compound (b) becomes 1:1.

The reaction product of the fluorinated compound (a) and the compound (c) with the polyisocyanate compound (b) may contain unreacted fluorinated compound (a) and compound (c), or some of isocyanate groups in the polyisocyanate compound (b) may be non-reacted. Preferably, however, the fluorinated compound (a) and the compound (c) are reacted at least 80% based on their total amount with isocyanate groups, and isocyanate groups in the polyisocyanate compound (b) are preferably reacted at least 80% thereof.

In order to produce a reaction product having no isocyanate group, it is necessary not only to produce a reaction product by adjusting the ratio of active hydrogen groups to isocyanate groups as mentioned above but also to detect isocyanate groups in the produced reaction product to ensure that isocyanate groups in the reaction product are preferably at most 5%, more preferably substantially 0. In a case where isocyanate groups are present in the reaction product, it is possible to produce a desired reaction product by using a method of adding the compound (c) or the like and reacting it until isocyanate groups will become no longer detected.

In the production of the reaction product, as a catalyst, a tertiary amine (such as triethylamine, bis(2-dimethylaminoethyl)ether or N,N,N',N'-tetramethylhexamethylenediamine), a metal salt of a carboxylic acid (such as potassium acetate or potassium 2-ethylhexanoate), or an organic metal compound (such as dibutyltin dilaurate) may, for example, be used.

Particularly preferred is triethylamine or dibutyltin dilaurate. The amount of the catalyst is preferably from 0.001 to 5 parts by mass per 100 parts by mass of the raw material mixture (the total of the fluorinated compound (a), the polyisocyanate compound (b) and the compound (c)).

The solvent for the reaction is not particularly limited so long as it has no active hydrogen group reactive with an isocyanate group, and it may, for example, be a halogen compound, a hydrocarbon, a ketone, an ester, an ether, a nitrogen compound or a sulfur compound.

The halogen compound may, for example, be a halogenated hydrocarbon or halogenated ether. The halogenated hydrocarbon may, for example, be a hydrochlorofluorocarbon, a hydrofluorocarbon or a chlorinated hydrocarbon. The hydrochlorofluorocarbon may, for example, be $CH_3CCl_2F$, $CHCl_2CF_2CF_3$ or $CHClFCF_2CClF_2$. The hydrofluorocarbon may, for example, be $CF_3CHFCHFCF_2CF_3$, $CF_3(CF_2)_4CHF_2$, $CF_3CF_2CF_2CH_2CH_2CH_3$, $CF_3(CF_2)_5CH_2CH_3$ or 1,1,2,2,3,3,4-hetapfluorocyclopentane.

The halogenated ether may, for example, be a hydrofluoroalkyl ether, a hydrofluoro(alkyl alkenyl ether), or a hydrofluorocyclic ether. The hydrofluoroalkyl ether may, for example, be a separated hydrofluoroalkyl ether or a non-separated hydrofluoroalkyl ether. The separated hydrofluoroether is a compound wherein a $R^F$ group is bonded to one side of the etheric oxygen atom, and an alkyl group is bonded to the other side. The non-separated hydrofluoroalkyl ether is a compound wherein a partially fluorinated alkyl group is bonded to each side of the etheric oxygen atom.

The separated hydrofluoroalkyl ether may, for example, be $CF_3CF_2CF_2CF_2OCH_3$, $(CF_3)_2CFCF_2OCH_3$, $CF_3CF_2CF_2CF_2OCH_2CH_3$, $(CF_3)_2CFCF_2OCH_2CH_3$, $CF_3CF_2CF(OCH_3)CF(CF_3)_2$, $CF_3CF_2CF(OCH_2CH_3)CF(CF_3)_2$ or $C_3H_7OCF(CF_3)CF_2OCH_3$. The non-separated hydrofluoroalkyl ether may, for example, be $CHF_2CF_2OCH_2CF_3$ or $CF_3CF_2CH_2OCF_2CHF_2$. The chlorinated hydrocarbon may, for example, be methylene chloride, chloroform, 1,1,1-trichloroethane, dichloroethylene, trichloroethylene or tetrachloroethylene.

The hydrocarbon may, for example, be an aliphatic hydrocarbon, an alicyclic hydrocarbon or an aromatic hydrocarbon. The aliphatic hydrocarbon may, for example, be pentane, 2-methylbutane, 3-methylpentane, hexane, 2,2-dimethylbutane, 2,3-dimethylbutane, heptane, octane, 2,2,4-trimethylpentane, 2,2,3-trimethylhexane, decane, undecane, dodecane, 2,2,4,6,6-pentamethylheptane, tridecane, tetradecane or hexadecane. The alicyclic hydrocarbon may, for example, be cyclopentane, methylcyclopentane, cyclohexane, methylcyclohexane or ethylcyclohexane.

The aromatic hydrocarbon may, for example, be benzene, toluene or xylene.

The ketone may, for example, be acetone, methyl ethyl ketone, 2-pentanone, 3-pentanone, 2-hexanone or methyl isobutyl ketone (hereinafter referred to as MIBK).

The ester may, for example, be methyl acetate, ethyl acetate, butyl acetate, or methyl propionate.

The ether may, for example, be an alkyl ether such as methyl tert-butyl ether, diisopropyl ether or cyclopentyl methyl ether, or a cyclic ether such as dioxane or tetrahydrofuran.

The nitrogen compound may, for example, be pyridine, N,N-dimethylformamide (DMF), N,N-dimethylacetamide or N-methylpyrrolidone. The sulfur compound may, for example, be dimethyl sulfoxide or sulfolane.

As the solvent for the reaction, chloroform, methyl ethyl ketone, MIBK, cyclohexanone or DMF is particularly preferred from the viewpoint of the dissolving properties. As the solvent for the reaction, one of the above-described solvents may be used alone, or two or more of them may be used in combination.

In the production method for the reaction product, the concentration of the starting material mixture in the solvent for the reaction is preferably from 5 to 100 mass %, more preferably from 10 to 90 mass %, particularly preferably from 20 to 80 mass %. The reaction is preferably carried out under an anhydrous condition in order to prevent side reactions.

The reaction temperature is usually from 0 to 200° C., preferably from 20 to 80° C. The reaction time is preferably from 1 to 200 hours.

Completion of the reaction can be ascertained by disappearance of a peak in the vicinity of 2,280 cm$^{-1}$ attributable to an isocyanate group by Fourier transform infrared spectrophotometer (FT-IR) measurement. For example, it can be ascertained by dropping one droplet of the reaction solution on a KBr window material, followed by transmission FT-IR measurement. Otherwise, completion of the reaction can be ascertained also by sampling a part of the reaction solution, removing the solvent by vacuum drying to obtain a solid of the reaction product, followed by reflection FT-IR measurement. The water/oil repellent agent of the present invention is preferably a reaction product having no isocyanate group (i.e. no isocyanate group is detected by this measurement).

<Water/Oil Repellent Composition>

The water/oil repellent composition of the present invention is a composition which comprises the above-described water/oil repellent agent and a solvent, and which may contain a surfactant and additives, as the case requires. The water/oil repellent composition of the present invention is preferably in such a form that the water/oil repellent agent is dissolved or dispersed as fine particles, in the solvent.

The water/oil repellent composition of the present invention may be produced by the following method (i), (ii), (iii) or (iv).

(i) A method wherein after obtaining a solution of the water/oil repellent agent by the above-described production method using the solvent for the reaction, other solvents and, as the case requires, additives, are added.

(ii) A method wherein after obtaining a solution of the water/oil repellent agent by the above-described production method using the solvent for the reaction, the water/oil repellent agent is separated, and a solvent and, as the case requires, additives are added to the water/oil repellent agent.

(iii) A method wherein after obtaining a solution of the water/oil repellent agent by the above-described production method using the solvent for the reaction, other solvents, surfactants and, as the case requires, additives are added, and as the case requires, the solvent is removed.

(iv) A method wherein after obtaining a solution of the water/oil repellent agent by the above-described production method using the solvent for the reaction, the water/oil repellent agent is separated, and a solvent, a surfactant and, as the case requires, additive are added to the water/oil repellent agent, and, as the case requires, the solvent is removed.

Specifically, the solvent in the present invention may, for example, be, in addition to the above-described solvent for the reaction, water, an alcohol, a glycol or a glycol ether. In a case where the water/oil repellent composition is a solution, a halogen compound, a ketone or an ester is particularly preferred from the viewpoint of the handling efficiency. In a case where the water/oil repellent composition is a dispersion, at least one medium selected from water, an alcohol, a glycol and a glycol ether is particularly preferred from the viewpoint of the dissolving properties and handling efficiency.

The alcohol may, for example, be methanol, ethanol, 1-propanol, 2-propanol, 1-butanol, 2-butanol, 2-methylpropanol, 1,1-dimethylethanol, 1-pentanol, 2-pentanol, 3-pentanol, 2-methyl-1-butanol, 3-methyl-1-butanol, 1,1-dimethylpropanol, 3-methyl-2-butanol, 1,2-dimethylpropanol, 1-hexanol, 2-methyl-1-pentanol, 4-methyl-2-pentanol, 2-ethyl-1-butanol, 1-heptanol, 2-heptanol or 3-heptanol.

The glycol or glycol ether may, for example, be ethylene glycol, ethylene glycol monomethyl ether, ethylene glycol monoethyl ether, ethylene glycol monobutyl ether, ethylene glycol monomethyl ether acetate, ethylene glycol monoethyl ether acetate, ethylene glycol monobutyl ether acetate, propylene glycol, as a glycol ether, propylene glycol monomethyl ether, propylene glycol monoethyl ether, propylene glycol dimethyl ether, dipropylene glycol, dipropylene glycol monomethyl ether, dipropylene glycol dimethyl ether, dipropylene glycol monoethyl ether, tripropylene glycol, tripropylene glycol monomethyl ether, polypropylene glycol or hexylene glycol.

The solid content concentration of the water/oil repellent agent in the solvent for the reaction is preferably from 5 to 100 mass %, more preferably from 10 to 90 mass %, particularly preferably from 20 to 80 mass %, in the solution (100 mass %), according to the above-described preferred production method for the water/oil repellent composition.

Here, the solid content concentration is a concentration including a surfactant (emulsifier) in addition to the water/oil repellent agent. Here, the solid content concentration is calculated from the mass of the water/oil repellent composition before heating and the mass after drying it for 4 hours by a convection dryer at 120° C.

In order to use a reaction solution containing the water/oil repellent agent obtained by the above-described production method for the reaction product of the present invention, as the water/oil repellent composition of the present invention, the water/oil repellent agent may be formulated by suitably adding a diluent component, etc. so that the solid content concentration becomes preferably from 0.05 to 10 mass %, more preferably from 0.1 to 5 mass %, as the water/oil repellent composition.

In a case where the water/oil repellent composition of the present invention is in the form of a dispersion, a common method may be employed wherein the water/oil repellent agent or a solution containing the water/oil repellent agent, a surfactant and optional components are weighed and uniformly stirred together with a proper amount of a solvent by a homomixer, a high pressure emulsifier or the like.

The average particle size of the water/oil repellent agent in the dispersion type water/oil repellent composition is preferably from 10 to 1,000 nm, more preferably from 10 to 300 nm, particularly preferably from 10 to 250 nm. When the average particle size is within such a range, it is not required to use a surfactant or the like in a large amount, the water repellency will be good, no color fading will occur when a dyed cloth is treated therewith, and dispersed particles may be present stably without sedimentation in the medium. The average particle size in the dispersion can be measured by a dynamic light scattering apparatus, an electron microscope or the like, and the above average particle size is a value measured by a dynamic light scattering apparatus.

Further, in order to disperse the water/oil repellent agent within the above-described preferred range of the particle size, the type and amount of a surfactant, or conditions such as the rotational speed of a homomixer or the pressure at the time of high pressure emulsification, may be adjusted.

The surfactant may be a hydrocarbon type surfactant or a fluorinated surfactant, which may, for example, be an anionic surfactant, a nonionic surfactant, a cationic surfactant or an amphoteric surfactant.

As the surfactant, it is preferred to use a nonionic surfactant and a cationic surfactant or an amphoteric surfactant, in combination or to use an anionic surfactant alone, in view of the dispersion stability, and it is particularly preferred to use a nonionic surfactant and a cationic surfactant in combination.

The total amount of surfactants is preferably from 1 to 20 parts by mass, more preferably from 1 to 15 parts by mass, to the water/oil repellent agent (100 parts by mass).

The additives include, for example, a penetrant, a defoamer, a water-absorbing agent, an antistatic agent, an antistatic polymer, an anticrease agent, a texture-adjusting agent, a film-forming assistant, a water-soluble polymer (such as polyacrylamide or polyvinyl alcohol), a thermosetting agent (such as a melamine resin, a urethane resin, a triazine ring-containing compound or an isocyanate-type compound), an epoxy curing agent (such as isophthalic acid dihydrazide, adipic acid dihydrazide, dodecanedioic acid dihydrazide, 1,6-hexamethylenebis(N,N-dimethylsemicarbazide) or 1,1,1',1'-tetramethyl-4,4'-(methylene-di-p-phenylene)disemicarbazide or spiroglycol), a thermosetting catalyst, a cross linking catalyst, a synthetic resin, a fiber-stabilizer or inorganic fine particles.

The amount of the additives is preferably from 0 to 50 mass %, more preferably from 0 to 20 mass %, based on the water/oil repellent agent (100 mass %).

The water/oil repellent composition of the present invention may contain a copolymer capable of exhibiting water repellency and/or oil repellency (e.g. a commercially available water repellent, a commercially available oil repellent, a commercially available water/oil repellent) or a water-repellent compound having no fluorine atom, as the case requires. The water-repellent compound having no fluorine atom may, for example, be a paraffin type compound, an aliphatic amide type compound, an alkylethylene urea compound or a silicone compound.

Articles to be treated with the water/oil repellent composition of the present invention are not particularly restricted, and various examples may be mentioned. Articles to be treated with the water/oil repellent composition of the present invention include, for example, fibers (natural fibers, synthetic fibers, mixed fibers, etc.), various fiber products, non-woven fabrics, resins, paper, leather, metals, stones, concrete, gypsum and glass. As preferred applications, synthetic leather, carpets, curtains, wallpaper and interior equipments for automobiles may, for example, be mentioned.

The treating method may, for example, be a method of coating or impregnating an article with the water/oil repellent composition by a known coating method, followed by drying. Further, antistatic finish, softening finish, antibacterial finish, deodorant finish or waterproofing finish may, for example, be carried out. The waterproofing finish may be processing to provide a waterproofing film. The waterproofing film may, for example, be a porous film made of an urethane resin or an acrylic resin, a non-porous film made of an urethane resin or an acrylic resin, a polytetrafluoroethylene film or a moisture-proofing film made of a combination thereof.

The water/oil repellent agent of the present invention comprises a reaction product obtained by reacting a fluorinated compound with a polyisocyanate compound. The environmental impact of the water/oil repellent agent of the present invention is low, and by treating an article with the water/oil repellent agent of the present invention, a sufficient water/oil repellency can be imparted. By treating the above-mentioned articles with the water/oil repellent composition of the present invention, a high quality water/oil repellency can be imparted to the articles.

EXAMPLES

Now, the present invention will be described in further detail with reference to Examples and Comparative Examples. However, it should be understood that the present invention is by no means restricted to such specific Examples.
[Preparation of Compound (a1)]

Into a reactor (internal capacity: 500 mL, made of glass) equipped with a stirrer, 4-hydroxybenzoic acid (135.0 g), 4-toluenesulfonic acid monohydrate (9.30 g) and $C_6F_{13}CH_2CH_2OH$ (533.8 g) were introduced in a nitrogen atmosphere and stirred. Then, heating was carried out so that the internal temperature of the reactor became 140° C., and the reactor was depressurized (0 to −0.05 MPa), and stirring was carried out for 6 hours while distilling water off. Further, the internal temperature of the reactor was lowered to 110° C., and the pressure was further reduced to distill off excess $C_6F_{13}CH_2CH_2OH$.

The obtained white solid was dissolved in 900 mL of ethyl acetate, then transferred to a separating funnel and washed twice with ion-exchanged water (1,200 mL), and the solvent in the ethyl acetate layer was distilled off, to obtain 460.8 g of the following compound (a1) (white solid). The yield was 98%.

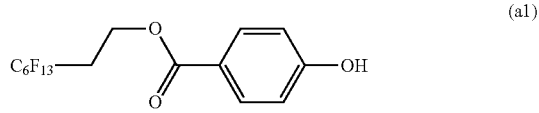
(a1)

The results of measurement of $^1$H-NMR of the obtained compound (a1) are shown below. Here, the respective measured values mean the measured values attributable to the groups shown in ( ) but in a case where such a group has a portion enclosed in [ ], the measured value means the measured value attributable to such a portion enclosed by [ ]. The same applies to the measured results of NMR shown in the following Examples.

$^1$H-NMR(solvent:$CD_3COCD_3$) δ(ppm): 2.81 (2H, m, —$CH_2CF_2$—), 4.62 (2H, t, —$COO[CH_2]CH_2$—), 6.94 (2H, d, Ph), 7.91 (2H, d, Ph), 9.21 (1H, s, —OH)

[Preparation of Compound (a2)]

Into a reactor (internal capacity: 500 mL, made of glass) equipped with a stirrer, ethyl 4-aminobenzoate (100.0 g), potassium carbonate (8.37 g) and $C_6F_{13}CH_2CH_2OH$ (440.8 g) were introduced in a nitrogen atmosphere and stirred. Then, heating was carried out so that the internal temperature of the reactor became 120° C., and the reactor was depressurized (0 to −0.05 MPa) and stirring was carried out for 12 hours while distilling ethanol off. The pressure was further reduced to distill off excess $C_6F_{13}CH_2CH_2OH$.

The obtained white solid was recrystallized from 1 L of methanol to obtain 205.0 g of the following compound (a2) (white solid). The yield was 70%.

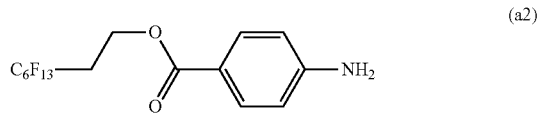
(a2)

The results of measurement of $^1$H-NMR of the obtained compound (a2) are shown in below.

$^1$H-NMR(solvent:$CD_3COCD_3$) δ(ppm): 2.77 (2H, m, —$CH_2CF_2$—), 4.57 (2H, t, —$COO[CH_2]CH_2$—), 5.47 (2H, s, —$NH_2$), 6.69 (2H, d, Ph), 7.76 (2H, d, Ph)

<FT-IR Measurement>

One droplet of a reaction solution was dropped on a KBr window material and set, followed by transmission FT-IR measurement. The reaction was completed at the time when a peak in the vicinity of 2,280 $cm^{-1}$ attributable to an isocyanate group completely disappeared, or such a peak substantially disappeared and no change in the peak was observed even if the reaction was further continued for 24 hours.

<$^1$H-NMR Measurement>

By carrying out $^1$H-NMR measurement of a solution after the reaction, the conversions of the fluorinated compound (a1) (Examples 1 to 4), the fluorinated compound (a2) (Examples 5 and 6) and $C_6F_{13}C_2H_4OH$ (Comparative Examples 1 and 2) were calculated. That is, relative to the chemical shift of a raw material, the chemical shift after reacted with an isocyanate appears mainly on a lower magnetic field side, and therefore, the conversion was obtained from the integrated intensity ratio of such signals.

For example, in Example 1, the chemical shift (in $CDCl_3$) attributable to the aromatic ring of the compound (a1) and the integrated intensity relative value are 6.9 ppm (integrated intensity relative value: 2) and 7.9 ppm (2), and the chemical shift attributable to the reaction product reacted with an isocyanate to form a urethane bond, and the integrated intensity relative value are 7.2 ppm (98) and 8.0 ppm (98), whereby the conversion is obtained to be 98%.

Example 1

Into a 100 mL glass reactor equipped with a stirrer, 2.77 g of Desmodur N-3200 (HDI biuret modified product, manufactured by Sumika Bayer Urethane Co., Ltd., isocyanate group content: 22.7 mass %), 7.23 g of compound (a1), 0.076 g of triethylamine as a catalyst, and 40.0 g of MIBK, were put and stirred for 48 hours at room temperature to obtain a reaction solution containing a fluorinated urethane compound as a reaction product. By the FT-IR measurement of the reaction solution after completion of the reaction, a peak attributable to an isocyanate group was found to have disappeared. Further, the conversion of the compound (a1) by $^1$H-NMR was 98%.

Comparative Example 1

Into a 100 mL glass reactor equipped with a stirrer, 3.37 g of Desmodur N-3200, 6.63 g of $C_6F_{13}C_2H_4OH$, 0.0013 g of dibutyltin dilaurate as a catalyst and 40.0 g of MIBK were put, heated to 80° C. and stirred for 3 hours to obtain a reaction solution containing a fluorinated urethane compound as a reaction product. By the FT-IR measurement of the reaction solution after completion of the reaction, a peak of an isocyanate group was found to have disappeared. Further, the conversion of $C_6F_{13}C_2H_4OH$ by $^1$H-NMR was 99%.

Example 2

Into a 100 mL glass reactor equipped with a stirrer, 2.90 g of Duranate THA-100 (HDI nurate modified product, manufactured by Asahi Kasei Chemicals, isocyanate group content: 21.2 mass %), 7.10 g of compound (a1), 0.074 g of triethylamine as a catalyst and 40.0 g of MIBK were put and stirred for 48 hours at room temperature to obtain a reaction solution containing a fluorinated urethane compound as a reaction product. By the FT-IR measurement of the reaction solution after completion of the reaction, a peak of an isocyanate group was found to have substantially disappeared. Further, the conversion of the compound (a1) by $^1$H-NMR was 95%.

Comparative Example 2

Into a 100 mL glass reactor equipped with a stirrer, 3.52 g of Duranate THA-100, 6.48 g of $C_6F_{13}C_2H_4OH$, 0.0012 g of dibutyltin dilaurate as a catalyst and 40.0 g of MIBK were put, heated to 80° C. and stirred for 3 hours to obtain a reaction solution containing a fluorinated urethane compound as a reaction product. By the FT-IR measurement of the reaction solution after completion of the reaction, a peak of an isocyanate group was found to have disappeared. Further, the conversion of $C_6F_{13}C_2H_4OH$ by $^1$H-NMR was 99%.

Example 3

Into a 100 mL glass reactor equipped with a stirrer, 2.16 g of COSMONATE M-200 (Polymeric MDI, manufactured by Mitsui Chemicals Inc., isocyanate group content: 31.5 mass %), 7.84 g of compound (a1), 0.082 g of triethylamine as a catalyst and 40.0 g of MIBK were put and stirred for 100 hours at room temperature to obtain a reaction solution containing a fluorinated urethane compound as a reaction product. By the FT-IR measurement of the reaction solution after completion of the reaction, a peak attributable to an isocyanate group was found to have substantially disappeared.

Further, the conversion of the compound (a1) by $^1$H-NMR was 90%.

Example 4

Into a 100 mL glass reactor equipped with a stirrer, 1.52 g of TDI (manufactured by Tokyo Chemical Industry Co., Ltd., isocyanate group content: 48.3 mass %), 8.48 g of compound (a1), 0.089 g of triethylamine as a catalyst and 40.0 g of MIBK were put and stirred for 100 hours at room temperature to obtain a reaction solution containing a fluorinated urethane compound as a reaction product. By the FT-IR measurement of the reaction solution after completion of the reaction, a peak attributable to an isocyanate group was found to have substantially disappeared. Further, the conversion of the compound (a1) by $^1$H-NMR was 92%.

Example 5

Into a 100 mL glass reactor equipped with a stirrer, 1.53 g of TDI, 8.47 g of compound (a2), and 40.0 g of MIBK were put, heated to 80° C. and stirred for 100 hours to obtain a reaction solution containing a fluorinated urea compound as a reaction product. By the FT-IR measurement of the reaction solution after completion of the reaction, a peak attributable to an isocyanate group was found to have substantially disappeared. Further, the conversion of the compound (a2) by $^1$H-NMR was 88%.

Example 6

Into a 100 mL glass reactor equipped with a stirrer, 2.06 g of MDI (manufactured by Tokyo Chemical Industry Co., Ltd., isocyanate group content: 33.6 mass %), 7.94 g of compound (a2), and 40.0 g of MIBK were put, heated to 80° C. and stirred for 100 hours to obtain a reaction solution containing a fluorinated urea compound as a reaction product. By the FT-IR measurement of the reaction solution after completion of the reaction, a peak attributable to an isocyanate group was found to have substantially disappeared. Further, the conversion of the compound (a2) by $^1$H-NMR was 85%.

<Evaluation 1 (Contact Angle)>

Sample plates were prepared by the following method by using each of the reaction solutions obtained in Examples 1 to 6 and Comparative Examples 1 and 2, and the water/oil repellency was evaluated.

[Preparation of Sample Plates]

The obtained reaction solution was diluted with acetone (Examples 1 to 4 and Comparative Examples 1 and 2) or DMF (Examples 5 and 6) to a solid content concentration of 1.0 mass % to obtain a treating liquid. Then, a coating film was formed on a glass plate by using each treating liquid by the following method, and the water/oil repellency of the coating film was evaluated. The results are shown in Table

TABLE 1

| | Evaluation 1 (contact angle) | | Evaluation 2 | |
|---|---|---|---|---|
| | Water | n-Hexadecane | Water repellency | Oil repellency |
| Example 1 | 112 | 70 | 80 | 7− |
| Example 2 | 118 | 81 | 80 | 7− |
| Example 3 | 112 | 73 | 80+ | 6 |
| Example 4 | 110 | 71 | 80− | 6 |
| Example 5 | 112 | 73 | 70+ | 6 |
| Example 6 | 118 | 76 | 70 | 6− |
| Comparative Example 1 | 64* | 58* | 70+ | 6 |
| Comparative Example 2 | 79* | 75 | 70 | 6 |

[Measurement of Contact Angle]

Using a cleaned glass plate as a substrate, the treating liquid obtained as described above, was applied thereon by a spin coating method for 10 seconds under a condition of 1,000 rpm. Then, by heat treatment at 120° C. for 60 minutes, a coating film was formed to obtain a test plate. With respect to all of the above treating liquids, test plates having such a coating film formed by using them, were prepared. By using each test plate thus obtained, the contact angles of water and n-hexadecane on such a coating film were measured, and thus, water and oil repellency of the coating film obtained from the treating liquid containing the copolymer prepared in each of the above Examples and Comparative Examples was evaluated. Here, the measurement of the contact angles was carried out by using CA-X manufactured by KYOWA INTERFACE SCIENCE CO., LTD.

In Table, values of the contact angle provided with * are not accurate values, since droplets on the coating film spread during the measurement. Further, what droplets spread means that the water repellency was insufficient.

It is evident from these results that a coating film having a high water repellency can be prepared with a treating liquid (water repellent composition) containing the water/oil repellent agent of the present invention, as compared to treating liquids (water/oil repellent compositions) containing the water/oil repellent agent of Comparative Examples which does not contain one of constituting components of the water/oil repellent agent of the present invention. Further, by using a treating liquid (water/oil repellent composition) containing the water/oil repellent agent of the present invention, a sufficient water/oil repellency can be imparted to an article, and environmental impact is also low.

<Evaluation 2>

With respect to each of the reaction solutions obtained in the above Examples 1 to 6 and Comparative Examples 1 and 2, a test cloth was prepared, and the water repellency and the oil repellency were evaluated by the following methods.

[Preparation of Test Cloth]

The obtained reaction solution was diluted with acetone (Examples 1 to 4 and Comparative Examples 1 and 2) or DMF (Examples 5 and 6) so that the solid content concentration became 0.6 g/L to obtain a test liquid. A polyester cloth was dipped in such a test liquid and squeezed so that the wet pick up became 100 mass %. It was dried at normal temperature for 24 hours and further dried at 170° C. for 60 seconds to obtain a test cloth.

[Evaluation of Water Repellency]

The water repellency of the test cloth was evaluated in accordance with JIS-L1092 spray test, and the water repellency was represented by the water repellency grade shown in Table 2. Here, the water repellency grade followed by +(-) indicates that such an evaluation is slightly higher (lower). The results are shown in Table 1.

TABLE 2

| Water repellency/oil repellency | State |
|---|---|
| 100 | There is no moisture or water droplet on a surface |
| 90 | There is slight water droplets on a surface |
| 80 | There is moisture on a part of surface |
| 70 | There is moisture on half of a surface |
| 50 | There is moisture on the entire surface |
| 0 | Completely soaked |

[Evaluation of Oil Repellency]

In accordance with the test method of AATCC-TM118-1966, each of the test solutions shown in Table 3 was placed in the form of droplets (diameter: about 4 mm) at two portions on the test cloth prepared as described above, and the oil repellency was represented by the oil repellency grade (No.) shown in Table 3 depending upon the soaked state after 30 seconds. Here, the oil repellency grade followed by +(-) indicates that such an evaluation is slightly higher (lower). The results are shown in Table 1.

TABLE 3

| Oil repellency grade No. | Test solutions | Surface tension mN/m (25° C.) |
|---|---|---|
| 8 | n-Heptane | 20.0 |
| 7 | n-Octane | 21.8 |
| 6 | n-Decane | 23.5 |
| 5 | n-Dodecane | 25.0 |
| 4 | n-Tetradecane | 26.7 |
| 3 | n-Hexadecane | 27.3 |
| 2 | 65 Parts of Nujol/35 parts by hexadecane | 29.6 |
| 1 | Nujol | 31.2 |
| 0 | Lower than 1 | — |

From these results, it is evident that when an article is treated with a water/oil repellent composition containing the water/oil repellent agent of the present invention, an excellent water/oil repellency can be imparted as compared with the water/oil repellent compositions containing the water/oil repellent agent of Comparative Examples which does not contain one of the constituting components of the water/oil repellent composition of the present invention.

INDUSTRIAL APPLICABILITY

The water/oil repellent agent or the water/oil repellent composition of the present invention is useful as a water/oil repellent agent for e.g. fiber products (clothing (sports wears, coats, jumpers, work clothes, uniforms, etc.), bags, carpets, curtains, wall papers, industrial materials, etc.), nonwoven fabrics, leather products, stone materials, concrete building materials, etc. Further, it is useful as a coating agent for filtration material or as a surface protective agent. Further, it is useful also for an application wherein it is mixed with e.g. polypropylene, nylon or polyester, followed by molding or forming into fibers to impart water/oil repellency.

This application is a continuation of PCT Application No. PCT/JP2011/062730, filed Jun. 2, 2011, which is based upon and claims the benefit of priority from Japanese Patent Application No. 2010-129012 filed on Jun. 4, 2010. The contents of those applications are incorporated herein by reference in its entirety.

What is claimed is:

1. A water/oil repellent agent which comprises a reaction product of a fluorinated compound (a) with a polyisocyanate compound (b), wherein the fluorinated compound (a) is represented by the formula:

$$R^f\text{—X-Ph-Y—Z}$$

wherein $R^f$ is a $C_{1-6}$ polyfluoroalkyl group,

X is a single bond, a $C_{1-4}$ alkylene group, $(CH_2)_m(CH_2)_n$ (each of m and n which are independent of each other, is an integer of from 0 to 4, with the proviso that m and n cannot both be zero) or $(CH_2)_pOCO$ (p is an integer of from 1 to 4), Ph is a phenylene group, Y is a single bond, a $C_{1-4}$ alkylene group or $(CH_2)_qO(CH_2)_r$ (q is an integer of from 0 to 4, and r is an integer of from 1 to 4), and Z is OH or NHR (R is a hydrogen atom or a $C_{1-6}$ alkyl group).

2. The water/oil repellent agent according to claim 1, wherein the reaction product has no isocyanate group.

3. The water/oil repellent agent according to claim 1, wherein the $R^f$ in the fluorinated compound (a) is a $C_{4-6}$ perfluoroalkyl group.

4. A water/oil repellent agent comprising a reaction product of a fluorinated compound (a) with a polyisocyanate compound (b), wherein the fluorinated compound (a) is a fluorinated compound represented by formula (a1) or (a2):

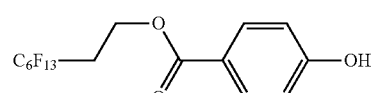

(a1)

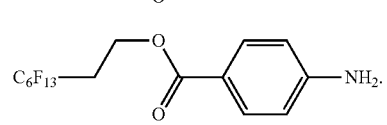

(a2)

5. The water/oil repellent agent according to claim 1, wherein the polyisocyanate compound (b) is hexamethylene diisocyanate or its modified product.

6. The water/oil repellent agent according to claim 1, which further contains a reaction product of a polyisocyanate compound (b) with a compound (c) having an active hydrogen group reactive with an isocyanate group, or a reaction product of a polyisocyanate (b) with the fluorinated compound (a) and a compound (c) having an active hydrogen group reactive with an isocyanate group.

7. A water/oil repellent composition which comprises the water/oil repellent agent as defined in claim 1 and a solvent.

8. The water/oil repellent composition according to claim 7, which has a solid content concentration of from 0.05 to 10 mass %.

9. The water/oil repellent agent according to claim 1, wherein X is a single bond, a $C_{1-4}$ alkylene group or $(CH_2)_p$ OCO (p is an integer of from 1 to 4).

10. The water/oil repellent agent according to claim 1, wherein X is $(CH_2)_p$OCO (p is an integer of from 1 to 4).

* * * * *